United States Patent [19]

Carroll et al.

[11] Patent Number: 5,170,055

[45] Date of Patent: Dec. 8, 1992

[54] RADIATION DETECTING BIOPSY PROBE

[75] Inventors: Robert G. Carroll, Largo, Fla.; Robin A. Wise, Jr., Morgan Hill, Calif.

[73] Assignee: Care Wise Medical Products Corporation, Morgan Hill, Calif.

[21] Appl. No.: 845,991

[22] Filed: Mar. 4, 1992

Related U.S. Application Data

[62] Division of Ser. No. 557,343, Jul. 25, 1990, Pat. No. 5,119,818.

[51] Int. Cl.⁵ ............................................... G01T 1/161
[52] U.S. Cl. ............................. 250/336.1; 250/363.10; 250/505.1; 128/659
[58] Field of Search ........... 250/336.1, 363.10, 363.02, 250/368, 505.1; 128/654, 659

[56] References Cited

U.S. PATENT DOCUMENTS

| | | | |
|---|---|---|---|
| 4,782,840 | 11/1988 | Martin, Jr. et al. | 128/559 |
| 4,893,013 | 1/1990 | Denen et al. | 128/559 |
| 4,959,547 | 9/1990 | Carroll et al. | 250/336.1 |
| 5,036,201 | 7/1991 | Carroll et al. | 128/659 |
| 5,119,818 | 6/1992 | Carroll et al. | 250/336.1 |

Primary Examiner—Carolyn E. Fields
Assistant Examiner—Drew A. Dunn
Attorney, Agent, or Firm—Caesar, Rivise, Bernstein, Cohen & Pokotilow, Ltd.

[57] ABSTRACT

A biopsy probe for detecting radiation emanating from a hidden source in a patient. The probe comprises a body member formed of a radiation blocking material and having a distal end portion and a proximal end portion. The proximal end portion is arranged to be held in the hand of a user. The probe comprises a radiation detector, e.g., a scintillation crystal, located within the distal portion of body member, a first radiation transparent window located at the distal end of the body member confronting the detector and through which radiation may pass to the detector, and a passageway extending through the distal end portion of the body member centered in the window and the detecting means. The passageway is arranged to guide a thin instrument, e.g., a biopsy needle, therethrough when the distal end portion is oriented in a direction toward the hidden source of radiation. A disposable cover/shield is also provided for releasable securement to the distal end of the probe to protect it from contamination. A collimator is also provided for releasable securement to the probe to reduce the probe's field of view.

16 Claims, 1 Drawing Sheet

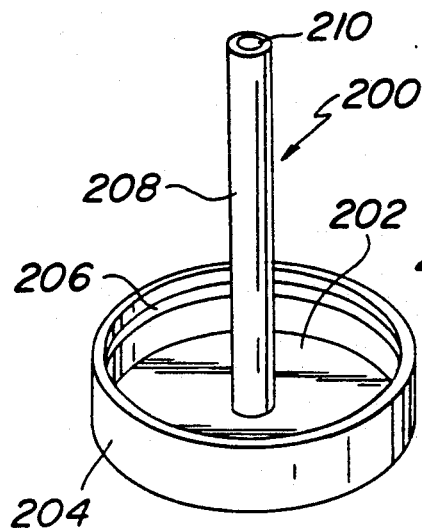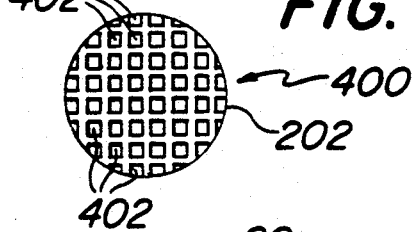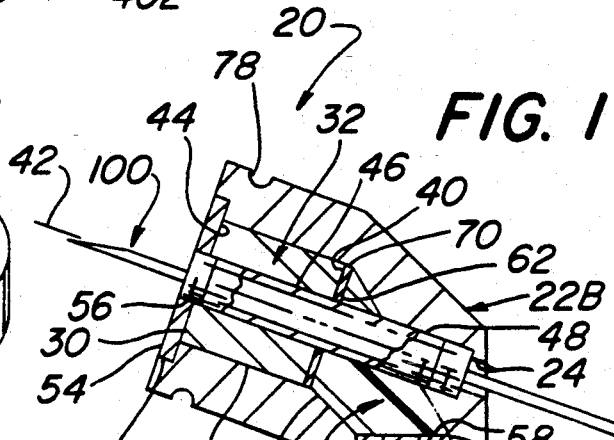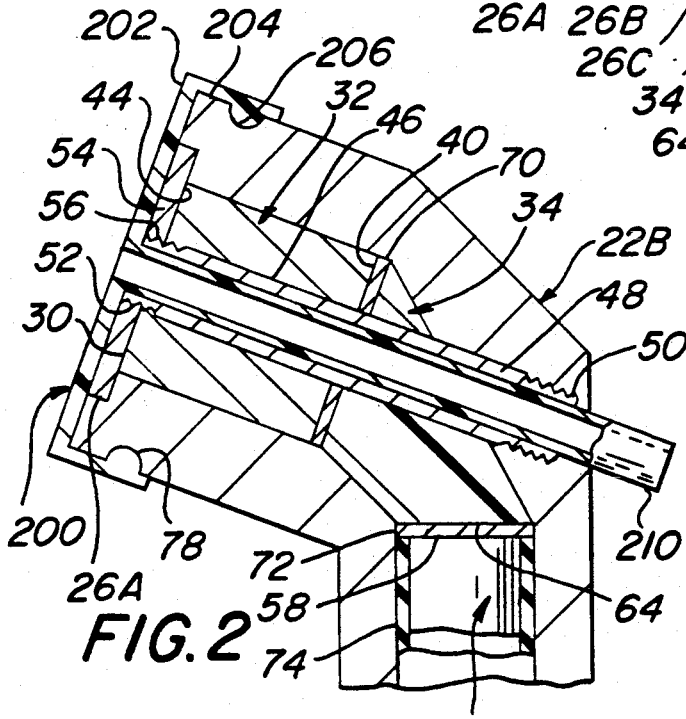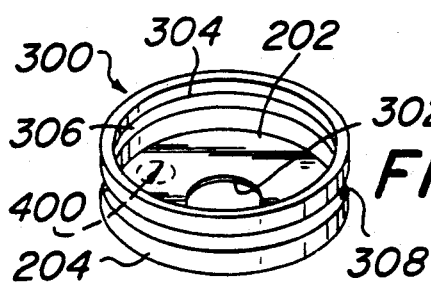

RADIATION DETECTING BIOPSY PROBE

This is a divisional of application Ser. No. 07/557,343 filed Jul. 25, 1990, now U.S. Pat. No. 5,119,818.

BACKGROUND OF THE INVENTION

This invention relates generally to probes for detecting radiation, and more particularly to radiation detecting probes for effecturating a biopsy of a portion of the body of a being.

The use of radioactive materials to tag tissue within a patient for effecting its localization and demarcation by radiation detecting devices has been disclosed in the medical literature for at least forty years. Significant developments in the localization and demarcation of tissue bearing radioactive isotope tags for diagnostic and/or therapeutic purposes have occurred since that time.

Thus, it is now becoming an established modality in the diagnosis and/or treatment of certain diseases, e.g., cancer, to introduce monoclonal antibodies tagged with a radioactive isotope (e.g., Indium 111, Technetium 99m, Iodine 123, and Iodine 125) into the body of the patient. Such monoclonal antibodies tend to seek out particular tissue, such as the cancerous tissue, so that the gamma radiation emitted by the isotope can be detected by a hand-held radiation detecting probe. Such a probe is disposed or held adjacent portion of the patient's body where the cancerous tissue is suspected to be in order to detect if any radiation is emanating from that site, thereby indicating that cancerous tissue is likely to be found there.

Prior art, hand-held, radiation detecting probes are commercially a available from the assignee of this invention, CareWise Medical Products, Inc. under the trademark OncoProbe, and from Neoprobe Corporation under the trademark NEOPROBE 1000. In co-pending U.S. patent applications Ser. Nos. 07/363,243 and 07/491,390, filed on Jun. 8, 1989 and Mar. 9, 1990, respectively, and assigned to the same assignee as this invention there are disclosed hand-held radiation detecting probes having collimating means to establish the field of view of the probe. In U.S. Pat. No. 4,801,803 (Denen et al.) there is also disclosed a hand-held radiation detecting probe.

In some medical applications it is desirable to conduct a biopsy of the area identified by the radiation detecting probe as being the source of the radiation, i.e., the cancer site. For example, the institution of treatment with a toxic chemotherapeutic agent usually requires a biopsy of the identified site to assure that cancer cells are, in fact, present at that site. Similarly, Monoclonal antibodies (MoAb) labeled with Technetium-99m or Indium-111 accumulate preferentially in specific cancers. Non-specific accumulation based on inflammation has been reported in the literature. Thus, biopsy of MoAb sites is frequently necessary for patient management. Biopsy of MoAb accumulation sites is essential to proving the specificity of any experimental MoAb diagnostic or therapeutic drug. The prior art radiation detecting probes while suitable for identifying the location of the radiation site are not conducive to facilitate the effectuation of a biopsy thereat.

OBJECTS OF THE INVENTION

It is a general object of this invention to provide a radiation detecting probe which overcomes the disadvantages of the prior art.

It is a further object of this invention to provide a radiation detecting probe which facilitates the effectuation of a biopsy at a site identified by the probe as being a source of radiation.

It is still a further object of this invention to provide a radiation detecting biopsy probe which is simple in construction and easy to use.

It is yet a further object of this invention to provide a disposable shield for use with a radiation detecting biopsy probe to enable the probe to be reused without requiring its resterilization.

SUMMARY OF THE INVENTION

These and other objects of this invention are achieved by providing a biopsy probe for detecting radiation emanating from a hidden source in a patient. The probe comprises a body member formed of a radiation blocking material and having a distal end portion and a proximal end portion. The proximal end portion is arranged to be held in the hand of a user. The distal end portion extends at an angle to the proximal end portion and is arranged to be directed toward a suspected location of the hidden source of radiation. The probe additionally comprises radiation detecting means located within the body member, a first radiation transparent window located at the distal end of the body member confronting the detecting means and through which radiation may pass to the detecting means, and a passageway extending through the distal end portion of the body member centered in the window and the detecting means. The passageway is arranged to guide a thin instrument, e.g., a biopsy needle, therethrough when the distal end portion is oriented in a direction toward the hidden source of radiation.

In accordance with another aspect of this invention a disposable shield is provided for the probe. The shield comprises a tubular member having a distal end from which a disk-like cover member projects outward radially. The tubular member is arranged to be located within the passageway in the distal end of the probe, with the disk-like cover member overlying and covering the distal end portion of said probe.

In accordance with another aspect of this invention collimators are provided for the probe. The collimators basically comprise a disk-like member having a central opening therein and mounting means. The disk-like member is arranged to overlie and cover the distal end portion of said probe, whereupon said disk-like cover member blocks some radiation from passing therethrough to establish a desired field of view.

DESCRIPTION OF THE DRAWINGS

Other objects and many attendant features of this invention will become readily appreciated as the same becomes better understood by reference to the following detailed description when considered in connection with the accompanying drawings wherein:

FIG. 1 is a longitudinal sectional view of a radiation detecting, biopsy probe constructed in accordance with the teachings of this invention;

FIG. 2 is an enlarged sectional view of the probe shown in FIG. 1 with a disposable cover/shield con- FIG. 3 is a perspective view of the cover/shield shown in FIG. 2;

FIG. 4 is a perspective view of a collimator for use with the probes of this invention; and FIG. 5 is an enlarged plan view of a portion of an alternative collimator, with said portion corresponding to the encircled portion of FIG. 4.

DETAILED DESCRIPTION OF THE PREFERRED EMBODIMENTS

Referring now to various figures of the drawing wherein like reference numerals refer to like parts there is shown at 20 in FIG. 1 a radiation detecting probe constructed in accordance with this invention. That probe is arranged to detect the presence of radiation emanating from a hidden source (not shown), such as tissue tagged with a radioactive isotope, and to provide electrical output signals indicative thereof, via a cable or wiring harness (not shown), to a conventional analyzer (not shown) or other conventional monitoring or imaging apparatus (not shown) so that the location of the source of radiation may be determined. As will be described in considerable detail later the probe is constructed with a passageway in it its head through which a conventional biopsy needle (or other small diameter biopsy instrument) may be inserted to penetrate the underlying tissue of the patient, so as to enable the site of the radiation to be examined.

The probe of this invention provides significant shielding for radiation from all directions other than that within its field of view (i.e., the solid angle of acceptance) by virtue of the materials used and the shape and organization of the probe. Thus, the probe 20 can be used with high energy radioisotopes, such as Indium 111. As will be appreciated by those skilled in the art Indium 111 has approximately ten times the energy of Iodine 125 (e.g., 247 KEV versus 25-30 kev). Without good shielding and collimation the use of such high energy materials would be precluded for use in some applications, e.g., detecting tagged cancerous tissue located near the liver, kidneys, or blood vessels, any of which locations would include significant accumulations of the isotope on a non-specific basis. The biopsy probe of the subject invention is designed to localize lymph node, containing a very small amount of radiation, e.g., a fraction of a microcurie to a few microcuries, lying adjacent to an organ containing several orders of magnitude more radiation.

The probe 20 shown in FIG. 1 basically comprises a body having a proximal handle portion 22A of a generally cylindrical shape and size to be readily held in one's hand. The handle portion 22A terminates in a distal portion or tip 22B extending at an acute angle, e.g., 70 degrees, to the longitudinal axis of the body portion 22A. The angular orientation of the tip 22B with respect to the hand grip portion 22A of the probe's body facilitates operator comfort and ease of aiming and biopsy needle insertion (as will be described later).

The probe body is formed of any suitable radiation blocking material, such as a tungsten alloy sold under the designation MIL-T-210140D by Teledyne Powder Alloys of Clifton, N.J. 07012.

The probe body includes a passageway 24 which extends through the probe's tip 22B concentric with the central axis 42 of the tip, and an internal bore 26 formed of various sections extending through the length of the probe's body. The passageway 24 serves as the access passageway for a biopsy needle 100 to be passed therethrough (as will be described later), while the internal bore 26 serves as the space in which the various components which make up the radiation, optical and electrical components of the probe are located.

As can be seen clearly in FIG. 1 the bore 26 is made up of six, longitudinally disposed sections, namely, 26A, 26B, 26C, 26D, 26E and 26F. Each of the bore sections 26A, 26B, 26D, 26E and 26F is cylindrical and of a respective, fixed inside diameter, whereas the bore section 26C is of a variable inside diameter (i.e., the bore section is conical).

The distal end of the bore section 26B defines a window 30 through which radiation is received by the probe's radiation detecting means when the probe is located at the suspected source of radiation.[1]

The details of the radiation detecting means will be described in detail later. Suffice it for now to state that such means preferably comprises a scintillation crystal 32, a light pipe 34, a photomultiplier tube 36, and a voltage divider circuit 38. The crystal is located within the second bore section 26B so that it confronts the window 30, whereupon the radiation blocking material of the probe's body contiguous with the window blocks the ingress of radiation to the crystal. Accordingly, the only radiation that reaches the crystal 32 is that radiation within the probe's normal solid angle of acceptance (field of view) as established by the window 30.

The crystal 32 may be of any suitable material, e.g., sodium iodide, mercuric iodide, bismuth germinate, etc. The crystal is a cylindrical body having a planar proximal end face 40 disposed perpendicularly to the longitudinal central axis 42 of the crystal, and a planar distal end face 44 disposed parallel to the proximal end face. A central bore 46 extends through the crystal between its end faces 40 and 44 concentric with the crystal's longitudinal central axis 42. The outside diameter of the crystal is just slightly less than the inside diameter of the bore portion 26B in the probe's tip, so that it snugly fits therein, allowing some space for reflective material on all crystal surfaces except at the light transmissive disc 70.

As can be seen clearly in FIG. 2 a tubular sleeve 48 is disposed within the central opening or bore 46 of the crystal 32. The sleeve includes a proximal or top end 50 including external threads thereon which mate with internal threads in the passageway 24 to hold the sleeve in place in the passageway. The sleeve serves to protect the crystal from damage when a biopsy needle 100 (or other instrument) is inserted through the passageway 24, and is preferably formed of stainless steel. In addition, the sleeve serves as one portion of a sealing system to prevent moisture or debris from gaining access to the crystal (the crystal being hygroscopic must be kept dry for maximum effectiveness).

The lower end 52 of the sleeve 48 extends out of the bore 46 in the crystal and into the bore section 22A. Like the upper end of the sleeve the lower end 52 of the sleeve 48 includes external threads thereon (See FIG. 2). These threads serve to secure a thin, sealing disk 54 in place within the bore section 22A. The disk 54 serves as a retaining member for the crystal and is of circular periphery, whose outside diameter just slightly less than the inside diameter of the bore section 22A to fit closely therein. The disk 54 also includes a central opening 56 which is internally threaded to mate with the external threads 52 on the sleeve's lower end, to thereby secure the disk in place.

The sealing disk 54 is formed of a radiation transmissive material, e.g., aluminum, and serves as another component of the sealing means to prevent moisture or debris from gaining ingress into the crystal 32. Preferably the disk 54 is locked in place with an adhesive, e.g., epoxy.

The photomultiplier tube 36 may be of any suitable type and basically comprises a cylindrical member, whose outside diameter is smaller than the inside diameter of the bore portion 26D to enable a shock absorbing material (to be described later) to be interposed therebetween. The photomultiplier tube 38 has an opposed pair of planar end faces 58 and 60, each of which is disposed perpendicular to the longitudinal axis of the tube. The end face 60 of the photomultiplier tube includes pins (not shown extending therefrom for electrical contact. The photomultiplier tube 36 is mounted within the bore portion 26 contiguous with the interface to the bore section 26C, so that its distal end face 58 is located at that interface.

The light pipe 34 is located within the bore section 26C and is formed of a good light transmissive material, e.g., plastic or glass, to carry light produced by the crystal 32 to the distal end of the photomultiplier tube 36. The light pipe 34 fills the bore section 26C and basically comprises a truncated, tilted, conical member including a distal end face 62 and proximal end face 64. The proximal end face 64 is planar and is oriented perpendicularly to the longitudinal axis of the bore section 26D holding the photodetector 36. The distal end face 62 of the light pipe 34 is also planar, but is disposed at the same acute angle, e.g., 70 degrees, to the end face 64 as the probe's tip 22B is to its handle portion 22A. Accordingly, when the light pipe 34 is in position its distal end face 62 is located immediately adjacent the proximal end face 40 of the crystal 34 to form a good light transmissive interface, while its proximal end face 64 is located immediately adjacent the distal end face 58 of the photomultiplier tube 36 to form a good light transmissive interface. Preferably light transmissive (optically transparent) shock absorbing disks 70 and 72 are disposed at respective interfaces. These disks enhance the probe's ability to withstand mechanical shocks. Light transmission through the interfaces may be expedited by the use of an optically index matched grease or adhesive (not shown) thereat.

It must be pointed out at this juncture that other detecting means can be utilized in lieu of the crystal 32 and the photomultiplier tube 36 described heretofore. Thus, any suitable solid state semiconductor detector material, e.g., cadmium telluride, silicon, mercuric iodide, etc., and an associated preamplifier may be used. In such a case the detector may be appropriately shaped, e.g., a ring or mosaic, to fit within bore sections 26B and 26C (the need for the light pipe having been obviated), while the preamplifier is located within the bore section 26D or within bore section 26C. Moreover, even when the detecting means is made up of a crystal and an associated photomultiplier (like that described heretofore), the crystal itself may be configured so that it fills the bore sections 26B and 26C, thereby obviating the need for the light pipe to carry light produced by the crystal to the photomultiplier tube.

The voltage divider 38 is housed within a cylindrical housing located within the bore section 26E distally of the photomultiplier tube's proximal end face 60. The voltage divider is held in place by a biasing spring (not shown). An electrical cable 66 extends from the voltage divider through bore section 26F. As can be seen the proximal end of the bore section 26F includes an internally threaded throat 68 which is adapted to receive a mating end cap (not shown). The cable 66 extends through a sealed opening in the end cap for connection to suitable monitoring apparatus (not shown).

As can be seen clearly in FIGS. 2 and 3 a shock absorbing material, e.g., foam, sleeve 74 is located within bore sections 26D and 26E to absorb any mechanical shocks, thereby protecting the photodetector 36 and the voltage divider 38. Such shock absorbing material may be located between the probe's body and all breakable internal components in the interests of ruggedizing the probe. Moreover, a ruggedized photomultiplier tube, such as that sold by Hamamatsu under the MIL designation R1635, may be used to achieve that end.

Operation of the probe 20 is as follows: The probe is adjacent the portion of the patient's body to be examined, so that the general location of the emanated radiation can be readily found. Once the probe is located so that it is centered directly over the apparent source of radiation, and with the free end of the probe tip 22B in contact with the patient's skin, a conventional biopsy needle 100 or other instrument is inserted through passageway 24 into the patient's body. Since the passageway 24 is axially aligned with the center of the detector 32, the biopsy needle 100 will be centered directly over the source of radiation. Thus, optimal biopsy localization of radio labeled tumors tagged with radio active MoAb agents can be achieved. Moreover, having the needle passageway 24 in the center of the probe optimizes radioactive shielding.

The 70° angle of the probe's tip 22B with respect to its body provides good ergonomics to enable the user's fingers to wrap comfortably around the probe's body while enabling the photomultiplier tube to be located as near as possible to the crystal and without the light pipe or photomultiplier tube interfering with the needle passageway 24.

In accordance with the preferred embodiment of the invention the needle passageway 24 is approximately 5 mm inside diameter and 7 mm outside diameter, while the crystal is approximately of 16 mm outside diameter.

In accordance with one preferred embodiment of this invention a disposal sterile cover/shield 200 is provided for the probe 20. This shield is arranged to be secured to the probe in such a manner that it covers all of the portions of the probe which may be contaminated by contact with any portion of the patient's body or by contact with the biopsy needle or other instrument through passageway 24. By so doing the need for repeated sterilizations of the probe may be reduced.

As can be seen in FIG. 3 the cover/shield 200 basically comprises a planar disk 202 which is of circular profile and includes a upwards extending flange 204 extending about the periphery thereof. The inside diameter of the flange 204 is equal to the outside diameter of the probe tip 22B. An annular, projection or bead 206 extends about the interior of the flange 204. A central tubular hub 208 projects perpendicularly from the interior surface of the disk 202. The outside diameter of tubular portion 20 is just slightly less than the inside diameter of the tube 48 in the passageway 24 so that it may fit therein.

The cover/shield 200 is arranged to be releasably secured to the probe tip via the ridge 206 cooperating with a groove 78 on the probe tip when the portion 208 is inserted within the probe's tube 48. As can be seen in FIGS. 1 and 2, the groove 78 extends about the periphery of the probe tip 22B adjacent the free end thereof.

The cover/shield 200 is preferably formed of a somewhat resilient material, such as plastic, so that it's flange 204 may flex slightly to enable it's annular ridge 206 to snap-fit into the groove 78 to expedite it's mounting onto the probe tip 22B.

The length of tubular portion 208 of the cover/shield 200 is sufficiently long so that when it is mounted on the probe tip 22B the free end 210 of the tubular portion 208 extends beyond the proximal end of passageway 24, thereby protecting the entire interior surface of passageway 24 from contact with the biopsy needle 100.

The probe 20 with the cover/shield 200 in place is used in the same manner as described heretofore.

After use the cover/shield 200 may be removed and disposed of, thereby readying the probe for mounting another and sterile cover/shield 200 for reuse without the need to resterilize the probe itself. Thus, with the use of the cover/shield the physician is free from the need to repetitively sterilize the probe when it is simply applied to sterilized prepared skin. Surgical operations inside body cavities will, however, require sterilization of the entire probe. However, even in such cases the covers 200 still can be helpful in preventing the spread of tumor cells and contamination of the instrument.

As should be appreciated from the foregoing the probe of this invention provides the physician or other user with means for readily determining the precise location of a radiation source within the body and also provide a means for guiding a biopsy needle or other instrument precisely to that site.

In order to provide a more narrow field of view of the probe an orifice restricting collimator 300 may be used with the probe. For example, as shown in FIG. 4 the collimator 300 may comprise a flat, washer-like member similar in construction to the cover/shield 200 shown in FIG. 3, except for a few structural differences to be described later. To expedite the description of the structure of the collimator its common structural features with those of the cover/shield 200 will be given the same reference numerals.

As can be seen clearly in FIG. 4 the collimator 300 does not include a central tubular portion 208, but instead includes a central opening or hole 302. In addition the collimator includes an annular groove 304 extending about the inner periphery of the flange 204 and having a resilient material, O-ring 306 retained in the groove. The central opening 302 in the disk-like portion 202 of the collimator serves as the passageway through which the radiation passes to the crystal 32, with the diameter of the opening being any predetermined size, e.g., 10, 12, 14 mm, etc., to provide the desired field of view. The collimator's disk portion 202 is formed of any suitable radiation blocking material, e.g., tungsten, and is of any suitable thickness, e.g., 2 mm, 6 mm, etc., to provide the desired amount of radiation blockage for Technetium 99m or Indium 111 without unduly increasing the size, weight or balance of the probe.

The O-ring 306 in the annular groove extending about the inner periphery of the collimator's flange 204 serves a similar function to the bead 206 of the shield/cover 200, i.e., it is arranged to be received within the annular groove 78 in the probe's tip, to releasably mounts the collimator in place thereon. When so mounted the collimator's central opening 302 is centered over the probe's tip and the central portion of the sealing disk 54, while its disk portion 202 overlies the remaining portion of the sealing disk 54 to block all radiation except that which passes through the opening 302. In so doing the collimator reduces the angle of acceptance of radiation reaching the crystal through the disk 54 and permits the sampling of a smaller volume of tissue, thereby allowing more precise definition of maximum or minimum areas of radioactivity. Moreover, the opening 302 serves as the passageway for the biopsy needle to pass therethrough.

In order to use the probe 20 having a collimator 300 mounted thereon with a shield/cover 200 like that described heretofore, the collimator includes mounting means for the shield/cover. In particular the mounting means comprises an annular groove 308 in the outer periphery of the collimator's flange 204 and into which the annular bead 206 of the shield/cover 200 may be disposed to mount the shield/cover on the collimator. In such an arrangement the diameter of the shield/cover's disk member 202 must be increased to accommodated the outside diameter of the collimator. In addition the tube 208 of the shield/cover must be lengthened to compensate for the thickness of the collimator's disk-like member.

As is known to those skilled in the art cancer lesions may be either "hot" or "cold" depending upon the tumor physiology and the radiopharmaceutical used. Collimators for restriction of field of view will be useful in "hot" lesions for more precise estimation of the hottest area. Such collimators are especially important in ascertaining the area of minimum radioactivity, when used to find "cold" lesions.

It should be pointed out at this juncture that the collimator can be constructed of plastic to provide fast electron and positron shielding for circumstances where the biopsy probe is used with beta emitters, such as phosphorous 32 or positron emitters, such as Fluorine 18.

It should also be pointed out that the detector means 32 may be comprised of a mosaic of solid state semiconductor elements (not shown). In such an arrangement each of these elements can be displayed separately on a visual display, such as a flat field LCD or plasma screen (not shown). Thus, the physician has access to an image of the biopsy field of view. The resolution of this image is limited by the number of mosaic elements and by the choice of collimation.

In FIG. 5 there is shown an enlarged portion of an alternative collimator 400 which is of particular utility when used with a probe whose detector is made up of a mosaic of detector elements. The collimator 400 is identical in construction to collimator 300 except that its entire disk-like member 202 includes a large plurality of identically sized, very small apertures 402 extending therethrough. As can be seen in FIG. 5 the apertures 402 are equadistantly spaced from one another and traverse the thickness, e.g., 6 mm, of the collimator's disk 202. Like collimator 300, collimator 400 includes a central opening 302. However that opening is smaller, e.g., is 7 mm, than the opening 302 in collimator 300 since the number, size and spacing of apertures 402 establish the field of view of the collimator 400. The opening 302 still serves as the passage for the biopsy needle to pass therethrough like in embodiment 300.

The collimator 400 is arranged to be mounted on the probe in the same manner as collimator 300 and may also be used with the sterile cover/shield 200 to effect parallel hole collimation of the entire image field of view.

Without further elaboration the foregoing will so fully illustrate our invention that others may, by applying current or future knowledge, adopt the same for use under various conditions of service.

What we claim is:

1. A disposable shield for use with a radiation detecting biopsy probe, said probe comprising a body member formed of a radiation blocking material and having a distal end portion and a proximal end portion, said proximal end portion being arranged to be held in the hand of a user, said distal end portion extending at an angle to said proximal end portion and arranged to be directed toward a suspected location of a hidden source of radiation, said probe additionally comprising radiation detecting means located within said body member, a first radiation transparent window located at the distal end of said body member confronting said detecting means and through which radiation may pass to said detecting means, and a passageway extending through said distal end portion of said body member centered in said window, said passageway being arranged to guide a biopsy instrument therethrough when said distal end portion is oriented in a direction toward said hidden source of radiation, said shield comprising a tubular member having a distal end from which a disk-like cover member projects outward radially, said tubular member being arranged to be located within said passageway in said distal end of said probe, with the disk-like cover member overlying and covering said distal end portion of said probe.

2. The shield of claim 1 wherein said probe additionally comprises an annular recess extending about said distal portion and wherein said disk-like cover member includes a flanged portion extending inward radially for engagement with said annular recess in said probe.

3. The shield of claim 1 wherein said shield is formed of a plastic material.

4. A collimator for use with a radiation detecting biopsy probe, said probe comprising a body member formed of a radiation blocking material and having a distal end portion and a proximal end portion, said proximal end portion being arranged to be held in the hand of a user, said distal end portion extending at an angle to said proximal end portion and arranged to be directed toward a suspected location of a hidden source of radiation, said probe additionally comprising radiation detecting means located within said body member, a first radiation transparent window located at the distal end of said body member confronting said detecting means and through which radiation may pass to said detecting means, and a passageway extending through said distal end portion of said body member centered in said window, said passageway being arranged to guide a biopsy instrument therethrough when said distal end portion is oriented in a direction toward said hidden source of radiation, said collimator comprising a disk-like member having a central opening therein and mounting means, said disk-like member being arranged to overlie and cover said distal end portion of said probe, whereupon said disk-like cover member blocks a portion of radiation from passing therethrough to establish a desired field of view of said probe.

5. The collimator of claim 4 wherein said disk-like member is formed of a radiation blocking material.

6. The collimator of claim 4 wherein said disk-like member is formed of a plastic material to provide fast electron and positron shielding.

7. The collimator of claim 4 wherein said probe additionally comprises an annular recess extending about said distal portion and wherein said mounting means of said collimator comprises a flanged portion having a surface extending inward radially for engagement with said annular recess in said probe.

8. The collimator of claim 7 wherein said surface of said flanged portion comprises an O-ring, and wherein said mounting means comprises an annular recess located within said flanged portion in which said O-ring is retained.

9. The collimator of claim 7 additionally comprising mounting means for mounting a disposable shield over said collimator.

10. The collimator of claim 9 wherein said mounting means comprises an annular groove extending about the outer periphery of said flanged portion of said collimator.

11. The collimator of claim 4 additionally comprising a plurality of apertures extending through said disk-like member to establish the field of view of said probe.

12. The collimator of claim 11 wherein said apertures are of uniform size and are equadistantly spaced from one another.

13. The collimator of claim 11 wherein said probe additionally comprises an annular recess extending about said distal portion and wherein said mounting means of said collimator comprises a flanged portion having a surface extending inward radially for engagement with said annular recess in said probe.

14. The collimator of claim 13 wherein said surface of said flanged portion comprises an O-ring, and wherein said mounting means comprises an annular recess located within said flanged portion in which said O-ring is retained.

15. The collimator of claim 4 wherein said disk-like member blocks radiation from passing therethrough except for radiation passing through said central opening.

16. The collimator of claim 15 wherein said central opening is of a predetermined size to establish a desired field of view.

* * * * *